United States Patent
Doebbeling et al.

(10) Patent No.: US 7,216,486 B2
(45) Date of Patent: May 15, 2007

(54) METHOD FOR OPERATING A TURBINE GROUP

(75) Inventors: Klaus Doebbeling, Windisch (CH); Ken-Yves Haffner, Baden (CH); Rolf Rüetschi, Nussbaumen (CH); Hanspeter Zinn, Baden-Ruetihof (CH)

(73) Assignee: ALSTOM Technology Ltd., Baden (CH)

( * ) Notice: Subject to any disclaimer, the term of this patent is extended or adjusted under 35 U.S.C. 154(b) by 0 days.

(21) Appl. No.: 10/894,031

(22) Filed: Jul. 20, 2004

(65) Prior Publication Data

US 2005/0028530 A1   Feb. 10, 2005

Related U.S. Application Data

(63) Continuation of application No. PCT/CH03/00045, filed on Jan. 22, 2003.

(30) Foreign Application Priority Data

Jan. 25, 2002 (DE) .............................. 102 03 102
Jun. 10, 2002 (CH) ................................. 0991/02

(51) Int. Cl.
F02C 3/22  (2006.01)
F02C 9/00  (2006.01)

(52) U.S. Cl. ................. 60/773; 60/39.465; 60/775; 60/776

(58) Field of Classification Search .......... 60/39.27, 60/39.281, 39.465, 773, 794, 775, 776
See application file for complete search history.

(56) References Cited

U.S. PATENT DOCUMENTS 4,594,510 A   6/1986 Brown et al.
6,082,092 A   7/2000 Vandervort
6,438,937 B1 *  8/2002 Pont et al. ................ 60/776
6,813,875 B2 * 11/2004 Inoue .................... 60/39.281

FOREIGN PATENT DOCUMENTS

DE   197 31 209 A1   1/1999

(Continued)

OTHER PUBLICATIONS

Search Report from PCT/CH 03/00045 (Apr. 24, 2003).

(Continued)

*Primary Examiner*—L. J. Casaregola
(74) *Attorney, Agent, or Firm*—Cermak & Kenealy, LLP; Adam J. Cermak (57) ABSTRACT

Relevant fuel-gas properties ($X_G$) are measured on an ongoing basis while a gas turbine group is operating. The $C_{2+}$alkane content of the fuel gas is of particular interest in this context, since it has a significant influence on the ignitability of the fuel gas in the combustion chamber. The operating parameters of the gas turbine group are acted on directly as a function of the measured fuel-gas properties. In particular, in the case of the example of a gas turbine group with sequential combustion, the distribution of the fuel mass flows ($\dot{m}_{EV}$, $\dot{m}_{SEV}$) between the combustion chambers (4, 8) of the gas turbine group is varied. Furthermore, if there is provision for inert media, such as water or steam, to be introduced, it is possible for the mass flow of inert media ($\dot{m}_{ST}$) to be controlled as a function of the measured fuel properties.

12 Claims, 5 Drawing Sheets

FOREIGN PATENT DOCUMENTS

| | | |
|---|---|---|
| DE | 199 21 981 A1 | 11/2000 |
| EP | 0 156 200 A1 | 10/1985 |
| EP | 0 554 095 A2 | 8/1993 |
| EP | 0 554 095 A3 | 12/1994 |
| EP | 1 022 514 A1 | 7/2000 |
| EP | 1 070 955 A2 | 1/2001 |
| WO | 91/06809 | 5/1991 |
| WO | 00/14451 | 3/2000 |
| WO | 00/52315 A2 | 9/2000 |
| WO | 00/52315 A3 | 9/2000 |
| WO | 02/14661 A1 | 2/2002 |
| WO | 03/062618 A1 | 7/2003 |

OTHER PUBLICATIONS

Search Report from CH 9912002 (Sep. 19, 2002).
IPER from PCT/CH 03/00045 (May 10, 2004).
Hoppe, M., Wolf, D. "IR instrument for gas property determination in industrial processes," IGRC 2001, Amsterdam, Netherlands, Nov. 6, 2001, (Ruhrgas AG, Germany).

* cited by examiner

METHOD FOR OPERATING A TURBINE GROUP

This application is a Continuation of, and claims priority under 35 U.S.C. § 120 to, International application number PCT/CH03/00045, filed 22 Jan. 2003, and claims priority under 35 U.S.C. § 119 to German application number 102 03 102.9, filed 25 Jan. 2002, and to Swiss application number 2002 0991/02, filed 10 Jun. 2002, the entireties of all of which are incorporated by reference herein.

BACKGROUND OF THE INVENTION

1. Field of the Invention

The present invention relates to a method for operating a gas turbine group.

2. Brief Description of the Related Art

The stability of combustion in modern premix burners of gas turbines is critically dependent in part on the ignitability of the fuel used, but also on other fuel properties, such as in particular the calorific value or the Wobbe index.

Premix burners of this type have been disclosed, for example, by EP 321 809, EP 780 629, WO 93/17279 or WO 92/19913. The various designs of burner are based on the common idea of introducing fuel into a swirling combustion-airstream and of generating an as far as possible homogenous and usually substoichiometric, lean fuel-air mix. When it is transferred into the combustion space, the swirling flow bursts open at a change in cross section, with the result that a backflow region which serves for flame stabilization is formed upstream of the burner mouth. The flame must not be stabilized too close to the burner mouth, in order to prevent excessive thermal loading of the burner. However, if the stabilization zone is too far downstream of the burner mouth, instability results.

The position of the combustion zone is also decisively dependent on the ignitability of the fuel used. This changes dramatically if, for example, a fuel gas contains high levels of higher saturated hydrocarbons, such as ethane, butane, propane, also known as $C_{2+}$alkanes. Since the fuel-air mix is supplied in premixed form, there is an acute risk of flashback to the burner. Component failure is then likely.

A similar problem also manifests itself when operating spontaneous-ignition combustion chambers of the type that are known from EP 669 500, for example in a gas turbine group with sequential combustion, as has been disclosed by EP 620 362. In this case too, flashback caused by a highly ignitable fuel gas can lead to major damage.

Furthermore, a change in the fuel-gas composition also has effects on the emissions and on combustion-chamber pulsations.

In addition to the $C_{2+}$-alkane content, the calorific value or Wobbe index also has an influence on the combustion behavior. In premix burner systems, this influence is primarily attributable to the changed pulse ratio of fuel gas and air at different Wobbe numbers. U.S. Pat. No. 6,082,092 describes controlling a variable fuel-gas preheating in such a way that the Wobbe index is kept constant. Control with a view to establishing a constant Wobbe index would also be possible by variable admixing of inert components in a closed-loop control circuit. DE 197 31 209 proposes keeping the Wobbe index constant when burning residual gases of highly varying composition by the controlled admixing of natural gas and nitrogen.

SUMMARY OF THE INVENTION

The invention relates to a method as initially mentioned. In one aspect the method is suitable for reacting to changes in the relevant fuel properties when a gas turbine group is operated with fuel gas. This reaction shall take place quickly enough to avoid a flashback, for example in the event of major variations in the $C_{2+}$-alkane content.

According to the invention a device for determining fuel-gas properties, which, in one embodiment, operates in real time without delay, is arranged at the fuel-gas feed to the gas turbine group. At least one fuel-gas property is determined in this way and fed into the control system of the gas turbine group. Then, targeted actions on parameters of the gas turbine group which influence the combustion are performed as a function of the fuel-gas property.

The relevant fuel property is in one embodiment the $C_{2+}$-alkane content of the fuel, which has a direct influence on the risk of flashback. In addition, it is also possible for the calorific value or the Wobbe index to be used directly as a supplemental fuel-gas property when the method is being carried out.

In an exemplary embodiment, an infrared measurement technique is used, as presented by Hoppe and Wolf in "IR Instrument For Gas Property Determination In Industrial Processes", IGRC 2001, Amsterdam, 6.11.2001. This allows the measurement to be carried out very quickly and for the measured values to be available in real time. In this context, it is proposed that the infrared absorption by the fuel gas be determined in two different spectral regions. It is proposed that the absorption be determined in a first spectral region around 3.5 μm, which reacts primarily to the ethane, propane and butane content, and in a second spectral region around 7.9 μm, where the absorption substantially reacts to the methane content of the measurement gas. The cross-sensitivity between the spectral regions is low and can easily be corrected if necessary. In this way, it is possible for the $C_{2+}$-alkane content to be determined continuously and rapidly. In principle, measurement only in the $C_{2+}$-alkane-sensitive spectral region around 3.5 μm is also sufficient to carry out the method according to the invention. This is quite sufficient for qualitative determination of a changed fuel-gas composition and for an appropriate reaction; measurement in both wavelength regions is more accurate and is in fact required for quantitative information to be obtained. In one embodiment of the method, the infrared absorption is additionally determined in a wavelength region around 4.3 μm, which reacts primarily to the $CO_2$ content. It is also possible to extend the method to other spectral regions which react sensitively to specific gas components. In a further preferred refinement, the thermal conductivity is measured as a measure of the nitrogen ($N_2$) content. Where appropriate, using cross-sensitivity correction algorithms, it is in this way possible to determine the fuel-gas composition very accurately, continuously and in real time. This also allows the calorific value or the Wobbe index to be determined.

The method according to the invention can for example be applied to a gas turbine group with sequential combustion, as disclosed by EP 620 362, and is moreover suitable if a self-igniting combustion chamber of the type known from EP 620 403 or EP 669 500 is provided as the second combustion chamber. Self-igniting combustion chambers are at particular risk of flashback, on account of the high mix temperature. With a gas turbine group of this type, it is possible to alter the distribution of fuel between the first and second combustion chambers as a function of the fuel properties, for example in such a manner that as the $C_{2+}$ content rises, the quantity of fuel fed to the second combustion chamber is reduced and the quantity of fuel fed to the first combustion chamber is increased accordingly.

It is known from EP 1 199 516 to make a central axial air flow variable in premix burners. In the context of the method according to the invention it is possible to control this axial flow as a function of the fuel properties determined. For example, as the $C_{2+}$-alkane content of the fuel gas rises, it is possible to make the axial flow more intensive, in order thereby to avoid the risk of flashback into the burner interior.

Premix burners of the types which are currently used often have a plurality of fuel feeds to which fuel can be supplied independently of one another, for example for the independent application of pilot fuel, which is burnt in a diffusion combustion mode, and premix fuel. Burners of this type are described, for example, by WO 01/96785, EP 193 838, EP 108 361, WO 00/12936, EP 945 677, or EP 321 809. The distribution of the fuel can be varied as a function of the measured fuel properties, in order on the one hand to ensure sufficient flame stability and at the same time to avoid flashback or component overheating and to keep the emission levels approximately constant.

In one embodiment of the invention, within a multi-burner system, with which the person skilled in the art will be familiar, the fuel distribution between individual burners and/or burner groups is varied as a function of the measured fuel properties.

It is also possible, as a function of the fuel properties, either for an inert medium to be introduced into the fuel gas, in which case this introduction may take place as close as possible to the gas turbine group to ensure short reaction times. Furthermore, an inert medium, such as steam or water, can be introduced into the combustion zone as a function of the measured fuel properties. The latter measure is suitable in particular for gas turbine groups which are already equipped with water and/or steam injection for the purpose of controlling emissions, since this measure has also proven eminently suitable for controlling the flame position and the combustion stability. In principle, by way of example, nitrogen or carbon dioxide would also be suitable inert media, but water and steam are generally more readily available.

A further control action possibility is for the gas turbine group to have means for cooling the working medium upstream of the compressor or in the compressor or between compressor stages. More intensive cooling reduces the temperature of the combustion air and thereby lowers the ignitability. Furthermore, it is known to realize the cooling by introducing a liquid, for example water, upstream of the compressor or into the compressor, in which case, for example, drops of water penetrate into the compressor and are evaporated during the compression. In recent times, this solution has become popular under the names wet compression, high fogging or overfogging, and has been described, for example, in U.S. Pat. No. 2,786,626, while FR 1,563,749 indicates the positive effects on the performance data of a gas turbine group. The humidification of the combustion air which results further reduces the ignitability.

In a further embodiment of the invention, a control action is performed directly in the protection system of the gas turbine group as a function of the measured fuel properties, in such a manner that, for example in the event of a certain $C_{2+}$-alkane concentration being exceeded, the supply of fuel or the set power value of the gas turbine group is reduced. Furthermore, if a further limit value is exceeded, it is possible to perform a protective action in such a manner that the gas turbine group is shut down immediately.

Of course, these various ways of acting on the gas turbine group as described above can also quite readily be combined with one another. Within the scope of the invention it is also possible, for the purpose of carrying out the control actions on the operation of the gas turbine group, to combine the measured fuel-gas properties with other measured values for the gas turbine group, such as pulsation and/or measured emission values, with a measured flame position, with material temperatures and the like.

BRIEF DESCRIPTION OF THE DRAWINGS

The invention is explained in more detail below on the basis of exemplary embodiments in conjunction with the drawings, in which.

The exemplary embodiments and the figures are to be understood as purely instructional and shall not be used to restrict the invention as described by the claims.

DETAILED DESCRIPTION OF THE PREFERRED EMBODIMENTS

Figure 1:
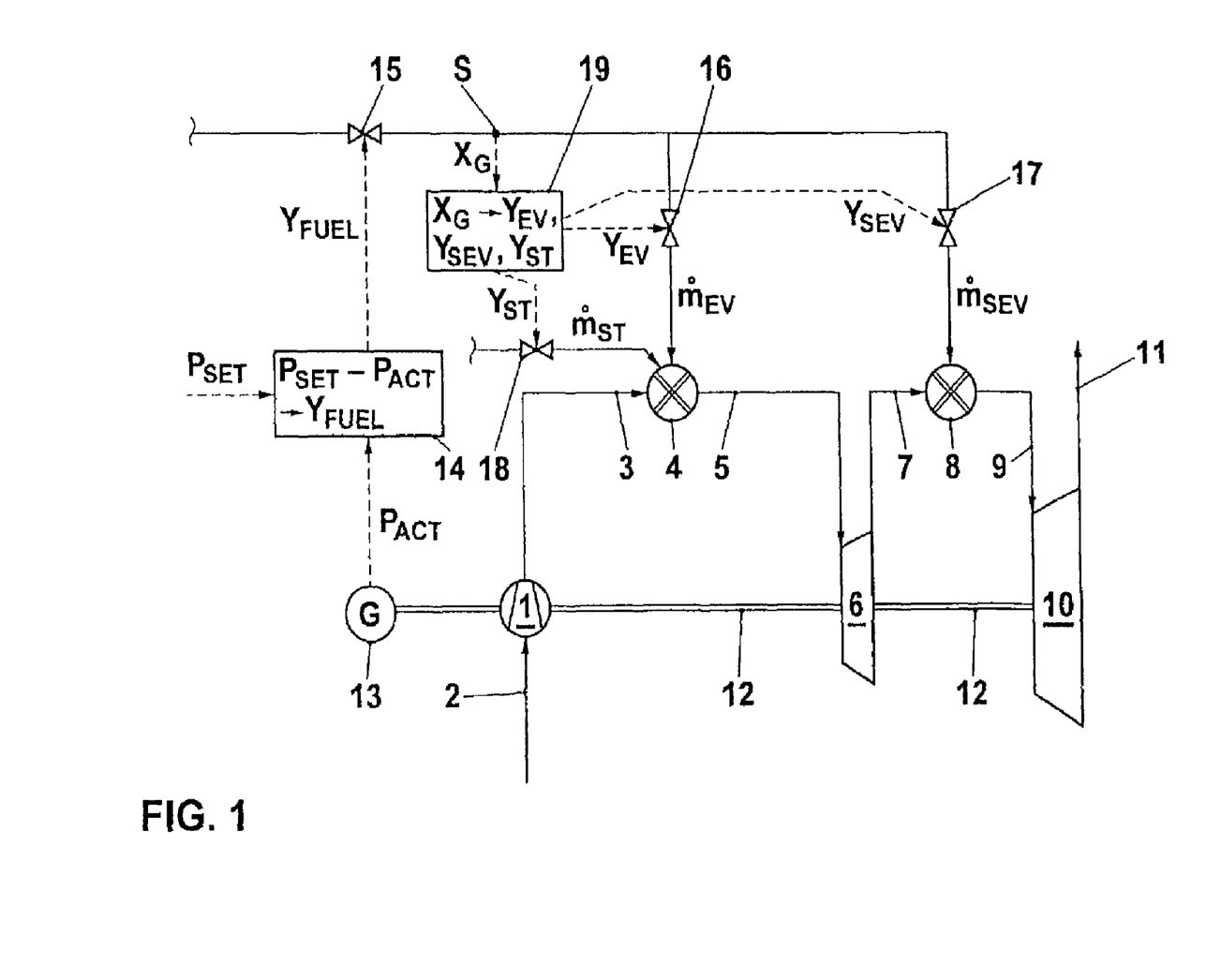
FIG. 1 shows a gas turbine group with sequential combustion for operation using the method according to the invention.

FIG. 1 shows a first example of how the method according to the invention can be carried out. A compressor 1, a first turbine 6 and a second turbine 10 are arranged on a common shaft 12. Furthermore, a generator 13 is coupled to the same shaft section. The compressor 1 sucks in ambient air 2, which is compressed and flows as compressed combustion air 3 to a first combustion chamber 4. This may typically, without implying any restriction, be a combustion chamber which is equipped with premix burners of the type described above. In the combustion chamber 4, a fuel quantity $\dot{m}_{EV}$ is added to the combustion air 3 and burnt. Hot, compressed flue gas 5 flows to the first turbine 6, where it is partially expanded, so as to output a shaft power, typically with a pressure ratio of 2. Partially expanded flue gas 7 emerges from the turbine 6 at still elevated temperature and flows to a second combustion chamber 8. This may, for example, be a combustion chamber of the type which is known from EP 669 500. A further fuel quantity $\dot{m}_{SEV}$ is added to the flue gas 7, which has an oxygen content of around 15% to 17%, and is burnt in the combustion chamber 8. The reheated flue gas 9 flows to a second turbine 10, and as it flows through the second turbine 10 is expanded again so as to output a shaft power, this time being expanded to approximately ambient pressure. This is basically a gas turbine group of the type which is known from EP 620 362, which document in this respect forms an integral part of the present description. The exhaust gas 11 is still at a temperature of a few hundred degrees centigrade, and this waste-heat potential can be utilized further in a manner which is known per se and is not shown here. The shaft power output of the turbines 6 and 10 is used to drive the compressor 1 and the generator 13. The generator 13 generates a useful electric power $P_{ACT}$. A useful power signal is compared with a desired power $P_{SET}$ in a first controller 14. A fuel mass flow control variable $Y_{FUEL}$ is formed from the control deviation $P_{SET}-P_{ACT}$ and acts on a fuel flow actuator 15, in this way controlling the overall supply of fuel to the combustion chambers 4, 8 of the gas turbine group. Two actuators 16 and 17 are responsible for dividing the overall fuel flow between the two combustion chambers 4 and 8.

The criteria according to which this fuel flow distribution is generally carried out have been described extensively in other publications. A sensor S for determining the fuel-gas property $X_G$ is arranged in the gas feed line. In a functional block 19, control variables $Y_{EV}$, $Y_{SEV}$ and $Y_{ST}$ are formed from the fuel properties $X_G$. The control variable $Y_{EV}$ acts on the actuator 16 and thereby controls the fuel quantity $\dot{m}_{EV}$ for the first combustion chamber 4. The control variable $Y_{SEV}$ acts on the actuator 17 and thereby controls the fuel quantity $\dot{m}_{EV}$ for the second combustion chamber 8. The control variable $Y_{ST}$ acts on an actuator 18 which meters a mass flow $\dot{m}_{ST}$ of inert medium, for example steam, to the first combustion chamber 4. Steam injection of this type into the combustion chamber is used, for example, for emission control as prior art with which the person skilled in the art will be familiar. According to the invention, the following control sequence is carried out: in a first operating state, the gas turbine group is set to its desired power. The total fuel flow is set by means of the actuator 15. The fuel is distributed between the two combustion chambers 4 and 8 by means of the actuators 16 and 17 in accordance with operating concepts which are described in detail elsewhere. The measuring device S measures the fuel properties $X_G$, for example the content of higher saturated hydrocarbons with two or more carbon atoms, known as the $C_{2+}$alkanes or saturated NMCH, continuously or quasi-continuously and virtually without any time delay. If the $C_{2+}$alkane content in the fuel increases, the ignitability of the fuel rises, and therefore so does the risk of a flashback, in particular in a combustion chamber of the self-igniting type. Therefore, if a rise in the $C_{2+}$alkane concentration in the fuel gas is measured, the control variables $Y_{EV}$ and $Y_{SEV}$ are used to act on the fuel distribution between the two combustion chambers 4 and 8, in such a manner that the mass flow of fuel $\dot{m}_{SEV}$ to the second combustion chamber is reduced and the mass flow of fuel $\dot{m}_{EV}$ to the first combustion chamber 4 is increased to the same extent. This eliminates the risk of a flashback in the second combustion chamber 8. However, depending on the operating state, the risk of a flashback in the first combustion chamber 4 then rises. Therefore, the control variable $Y_{ST}$ is used to open the actuator 18, and a quantity of steam $\dot{m}_{ST}$ is introduced into the first combustion chamber 4, with the result that the higher ignitability of the combustion chamber is taken into account here too. If the $C_{2+}$alkane content of the fuel gas exceeds a limit value, furthermore, control action is taken on the protection systems of the gas turbine group, which are not shown but with which the person skilled in the art will be familiar, for example by the power set value $P_{SET}$ being automatically reduced. Furthermore, if a further limit value is exceeded, the gas turbine group can be quickly shut down.

Figure 2:
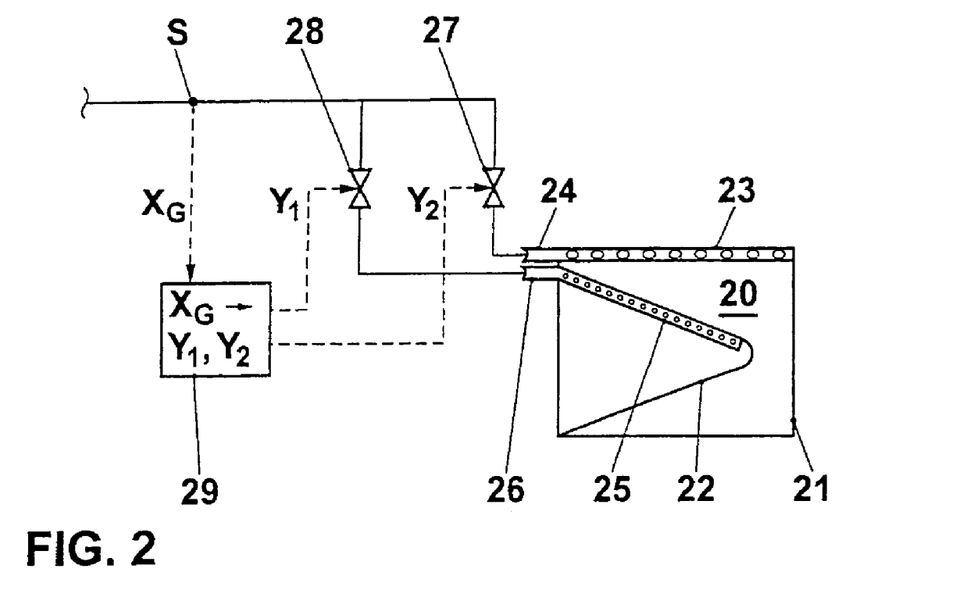
FIG. 2 shows a first type of burner and its operation in accordance with the method of the invention.

FIG. 2 shows a first burner for a gas turbine group of a design which is known from WO 01/96785 in conjunction with an operating method according to the invention. The burner 20 comprises a cylindrical swirl generator 21 and a conical inner body 22. Furthermore, the burner has two different groups of fuel-gas openings 23 and 25, which can be supplied with fuel independently of one another and are supplied with fuel through separate fuel-gas connections 24 and 26. Fuel is metered to the fuel-gas openings 23 and 25 by two actuators 27 and 28, the feedlines of which branch off from a common fuel-gas feedline in which a measuring device S for determining the fuel-gas properties $X_G$ is arranged. Working on the basis of the fuel properties $X_G$, control variables $Y_1$ and $Y_2$ which act on the actuators 27 and 28 are formed in a functional block 29. When the burner illustrated is operating in a combustion chamber of a gas turbine group, the actuators 27 and 28 are controlled on the basis of specific criteria in order thereby to in each case achieve a favorable distribution of the fuel quantity between the groups of fuel-gas openings 23 and 25. The sensor S continuously determines the fuel-gas properties $X_G$, and in the event of corresponding changes, control actions are taken on the actuators 27 and 28 in order to change the fuel distribution within the burner in a suitable way.

Figure 3:
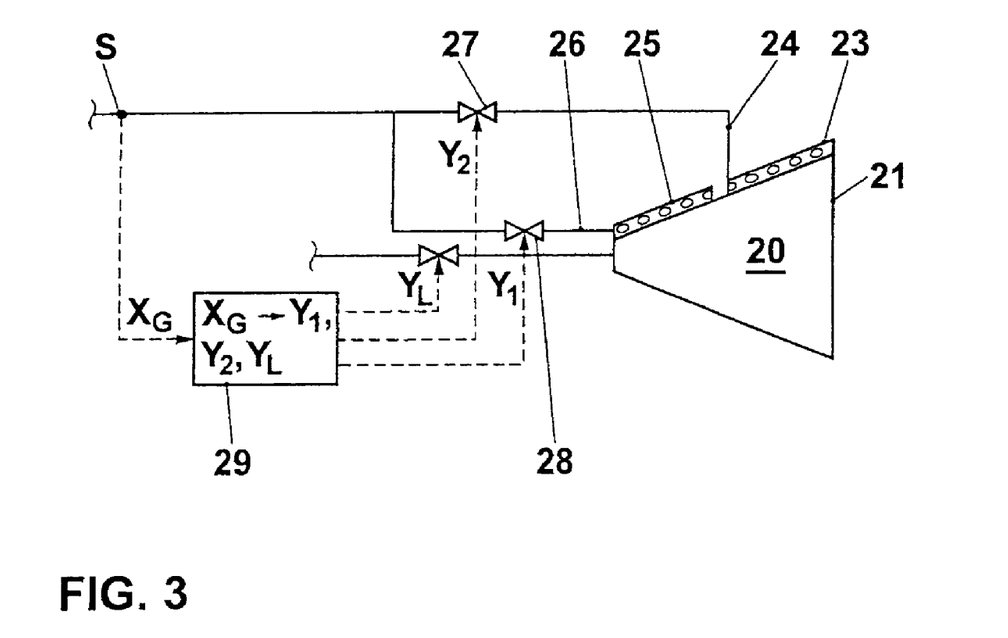
FIG. 3 shows a second type of burner and its operation in accordance with the method of the invention.

FIG. 3 shows a further burner design which is known from WO 01/96185. The burner 20 has a conical swirl generator 21, as disclosed by EP 321 809. The burner has two groups 23 and 25 of fuel-gas openings. The groups can be supplied with fuel gas independently of one another via the feed lines 24 and 26 having the actuators 27 and 28. Upstream of the actuators 27 and 28, the connections branch off from a common gas supply line. Furthermore, the burner illustrated has a variable central axial air feed, as disclosed by EP 1 199 516. A measuring device S which determines the fuel-gas properties and supplies them to the unit 29 is arranged in the gas supply line. For operation inside the combustion chamber of a gas turbine group, the quantitative distribution of fuel between the groups 23 and 25 and the axial air flow are preselected in a suitable way. In the event of changes to the fuel-gas properties, the control variables $Y_1$ and $Y_2$ are used to influence the fuel distribution, and the control variable $Y_L$ is used to influence the axial air flow, as a function of the measured fuel-gas properties $X_G$. In particular as the $C_{2+}$-alkane content rises, the central axial air flow can be boosted by means of the control variable $Y_L$. In this way, the flame stabilization takes place further downstream of the burner mouth, and the risk of flashback is avoided.

Figure 4:
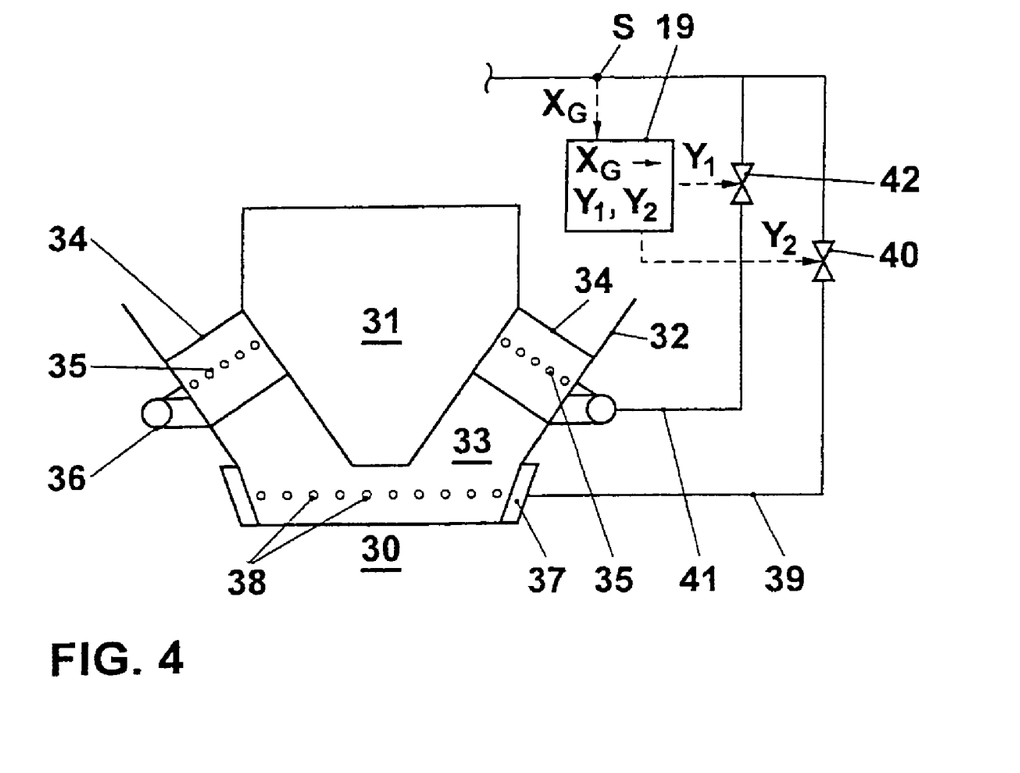
FIG. 4 shows a third type of burner and its operation in accordance with the method of the invention.

FIG. 4 shows a burner which is known from WO 00/12936. This burner has two groups of fuel-gas openings 35 and 38, which can be supplied with fuel independently of one another via the annular passages 36 and 37, the feedlines 39 and 41 and the actuators 40 and 42. In a similar way to in the examples described above, the fuel-gas properties $X_G$ are determined, and the fuel distribution between the groups of fuel-gas openings 35 and 38 is influenced as a function of these fuel-gas properties in a similar manner to the procedure described above.

Figure 5:
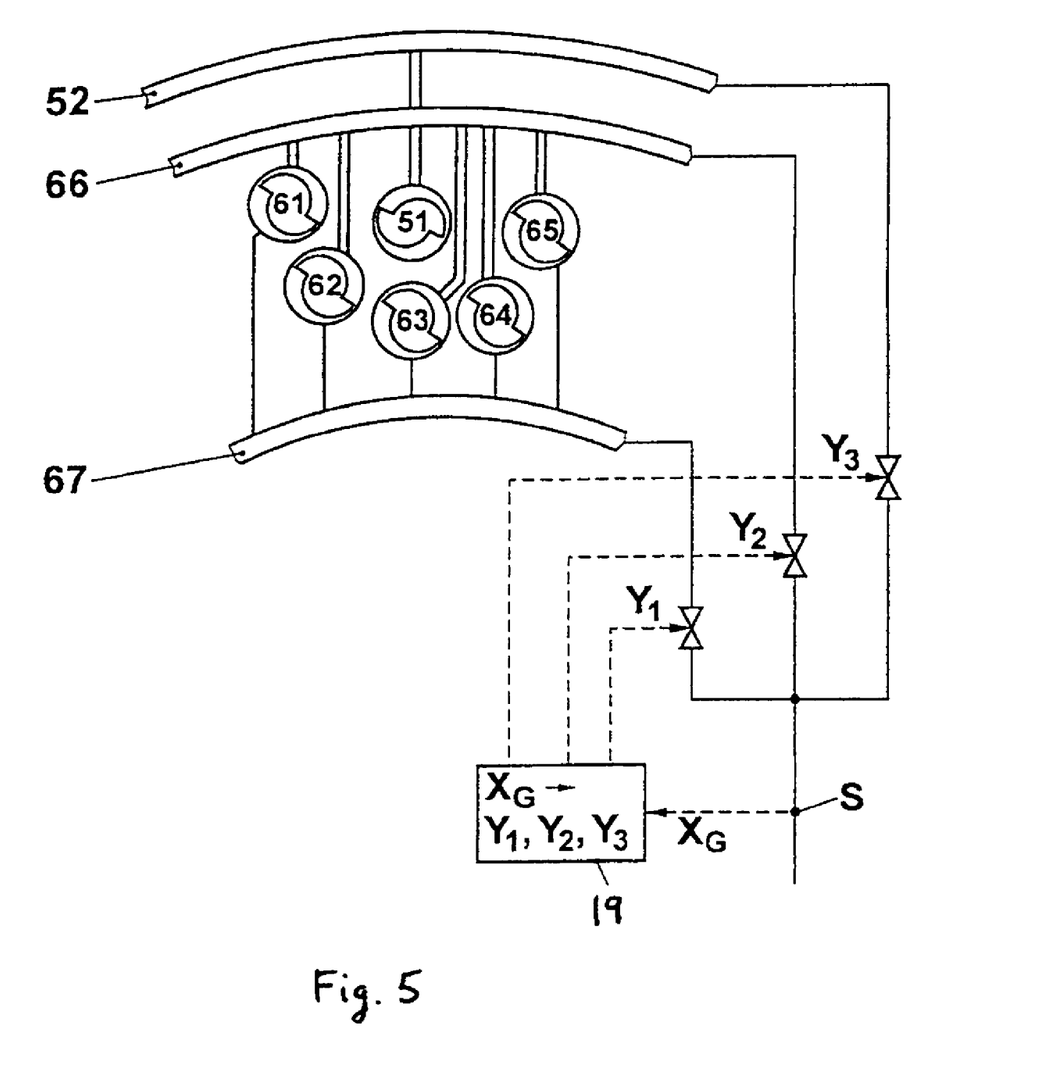
FIG. 5 shows a multiburner system and its operation in accordance with the method of the invention.

FIG. 5 illustrates an excerpt from a multiburner system of a combustion chamber of a gas turbine group. The burner 51 is connected to a ring line 52. Fuel-gas openings for premix operation of the burner are fed via this ring line. The burners 61, 62, 63, 64, 65 are connected to fuel lines 66 and 67. First groups of fuel-gas openings of the burners 61, 62, 63, 64, 65 are supplied with fuel gas through the ring line 66; these fuel-gas openings are designed, for example, for the injection of gas for premix combustion. Further fuel-gas openings of the burners 61, 62, 63, 64, 65 are supplied with fuel gas through the ring line 67; these further fuel-gas openings are designed, for example, for the introduction of a fuel gas which is to be burnt in a diffusion combustion mode. The ring lines are for their part connected to a common gas supply. The fuel-gas mass flows which flow to the individual ring lines or their associated burners or burner groups or fuel-gas openings can be set independently of one another by means of actuators. An operating concept of this type is known, for example, from gas turbine GT13E2 produced by the assignee, with the distribution of the fuel mass flows between the ring lines being effected substantially as a function of the power. According to the invention, a sensor S for determining the fuel-gas properties $X_G$ is arranged in the common fuel-gas line. Control variables $Y_1$, $Y_2$ and $Y_3$ which act on the fuel-flow actuators of the ring lines are formed from the fuel-gas properties $X_G$. In this way it is once again possible to act on the distribution of the fuel within the burner system in the event of a change in the fuel-gas properties.

Figure 6:
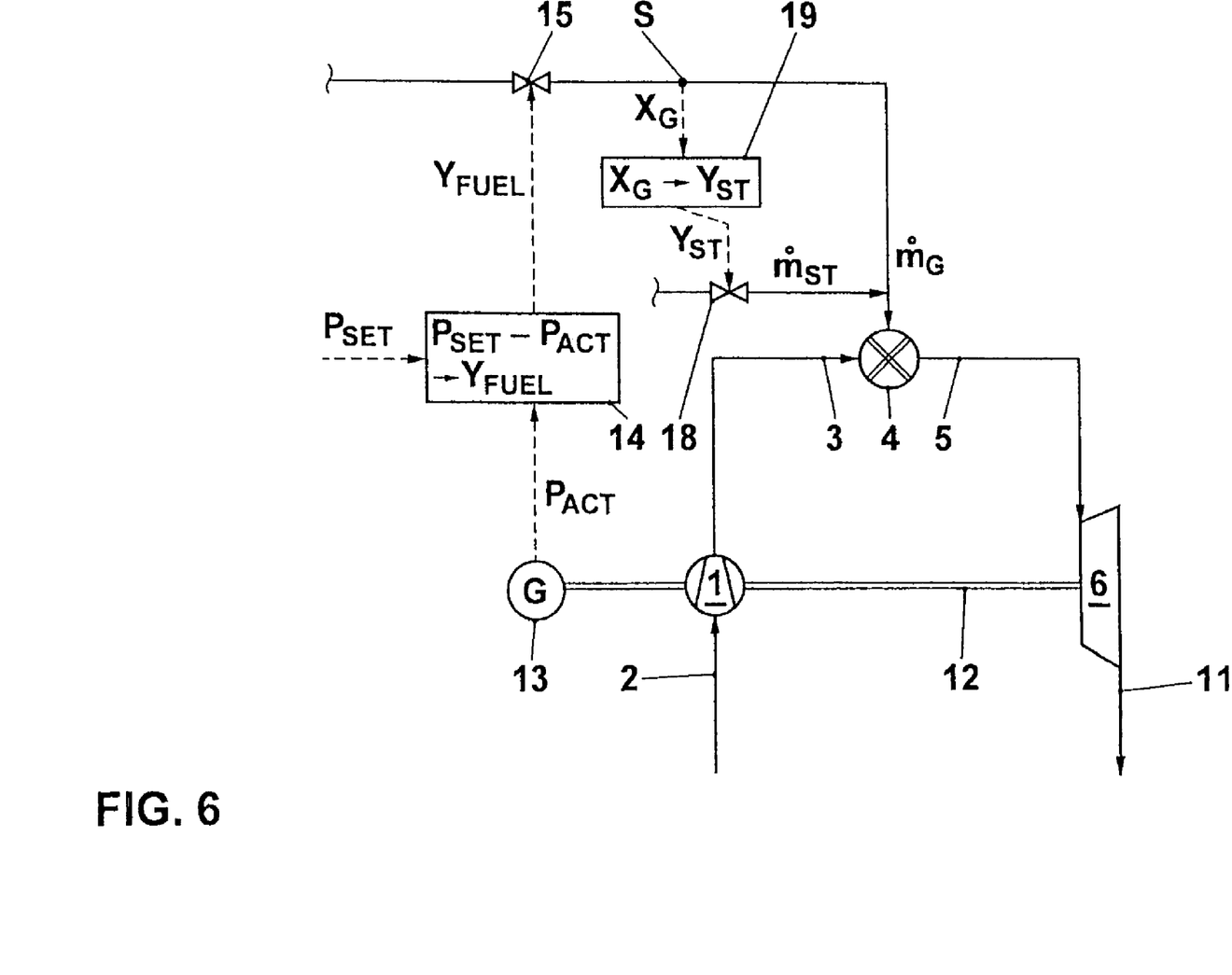
FIG. 6 shows a further example of a gas turbine group which is operated in accordance with the invention.

Finally, FIG. 6 shows a gas turbine group whose function need not be explained further in light of the above statements. A fuel-flow controller 14 uses the fuel-flow control variable $Y_{FUEL}$ and the fuel-flow actuator 15 to control the mass flow of fuel to the combustion chamber 4 in such a way that the control deviation in the power, $P_{SET}-P_{ACT}$ is precisely compensated for and therefore disappears. A measuring device S for determining the fuel-gas properties $X_G$ is arranged in the fuel-gas line. A control variable $Y_{ST}$ which acts on the position of the actuator 18 is formed as a function of the determined values. This position in turn determines a mass flow of inert medium $\dot{m}_{ST}$ which is admixed to the fuel gas upstream of its introduction into the combustion chamber 4. If, for example, the NMCH content of the fuel gas and/or its calorific value then rises, at this location steam or another inert medium is added in order to reduce the ignitability or calorific value of the gas. The measuring location is arranged upstream of where the medium is added thus accelerating the control. Therefore, a change in the fuel-gas properties is recorded a certain time before such a change actually becomes active in the combustion chamber. However, since the location where the inert medium is added is arranged significantly closer to the combustion chamber, the time required for the control action to become active is short. This means that the method is perfectly suitable for initiating countermeasures to prevent the threat of damage to the machine as a result of the change in fuel-gas composition.

Of course, the exemplary embodiments described can only cover a small part of the invention as characterized by the claims. In particular, the method variants presented can be employed in a wide range of appropriate combinations. It would also be possible to combine the measured fuel properties with pulsation and/or emission measured values, measured flame positions, material temperatures and the like to form the abovementioned control variables. In view of the above disclosure, a wide range of possible method variants, which are in each case to be selected on a machine-specific basis, will become apparent to the person skilled in the art.

LIST OF DESIGNATIONS

1 Compressor
2 Intake air
3 Compressed air, combustion air
4 Combustion chamber
5 Compressed flue gas
6 Turbine
7 Partially expanded flue gas
8 Combustion chamber
9 Reheated flue gas
10 Turbine
11 Exhaust gas
12 Shaft
13 Generator
14 Controller
15 Actuator
16 Actuator
17 Actuator
18 Actuator
19 Functional block
20 Burner
21 Swirl generator
22 Inner body
23 Group of fuel-gas openings
24 Fuel-gas feed
25 Group of fuel-gas openings
26 Fuel-gas feed
27 Actuator
28 Actuator
29 Functional block
30 Burner
31 Burner inner body
32 Burner outer casing
33 Burner annular space
34 Combustion-air guide vane, swirl generator
35 Fuel-gas openings
36 Fuel-gas ring line
37 Fuel-gas annular space
38 Fuel-gas openings
39 Fuel-gas line
40 Actuator
41 Fuel-gas line
42 Actuator
51 Burner
52 Fuel-gas ring line
61 Burner
62 Burner
63 Burner
64 Burner
65 Burner
66 Fuel-gas ring line
67 Fuel-gas ring line
$\dot{m}_{EV}$ Fuel-gas mass flow
$\dot{m}_{SEV}$ Fuel-gas mass flow
$\dot{m}_G$ Fuel-gas mass flow
$\dot{m}_{ST}$ Inert medium mass flow, steam mass flow
$P_{ACT}$ Useful power
$P_{SET}$ Set power
S Measuring device for the fuel-gas properties
$X_G$ Measurement signal for fuel-gas properties
$Y_1$ Control variable
$Y_2$ Control variable
$Y_3$ Control variable
$Y_{FUEL}$ Fuel quantity control variable
$Y_{EV}$ Control variable
$Y_{SEV}$ Control variable
$Y_{ST}$ Control variable While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for operating a gas turbine group, the gas turbine group including a fuel gas supply line and a device for determining fuel gas properties arranged in said fuel gas supply line, the method comprising:
   determining at least one fuel gas property;
   feeding the determined fuel gas property to a control system of the gas turbine group;

performing control action on the operation of the gas turbine group dependent on the determined fuel gas property, the control action being performed on at least one selected from the group consisting of the distribution of a fuel gas mass flow between different fuel gas outlet openings, a combustion air supply of burners of the gas turbine group, and the injection of inert media into a gas turbine group working fluid; and selecting the content of $C_{2+}$-alkanes as the fuel gas property.

2. The method of claim 1, comprising:
selecting the heating value as a supplemental fuel gas property.

3. The method of claim 1, comprising:
selecting the Wobbe-index as a supplemental fuel gas property.

4. A method for operating a gas turbine group, the gas turbine group including a fuel gas supply line and a device for determining fuel gas properties arranged in said fuel gas supply line, the method comprising:
determining at least one fuel gas property;
feeding the determined fuel gas property to a control system of the gas turbine group;:
performing control action on the operation of the gas turbine group dependent on the determined fuel gas property, the control action being performed on at least one selected from the group consisting of the distribution of a fuel gas mass flow between different fuel gas outlet openings, a combustion air supply of burners of the gas turbine group, and the injection of inert media into a gas turbine group working fluid;
selecting a first infrared spectral range such that absorption in said first spectral range is effected by $C_{2+}$-alkanes;
selecting a second infrared spectral range such that absorption in said second spectral range is the effected by methane;
measuring the infrared absorption in at least said first and second spectral ranges; and
determining the fuel gas properties from the measured infrared absorption.

5. The method of claim 4, comprising:
selecting a third spectral range such that the absorption in said third spectral range is effected by carbon dioxide; and
measuring the infrared absorption in said third spectral range.

6. The method of claim 4, comprising:
measuring the thermal conductivity of the fuel gas.

7. The method of claim 1 comprising:
feeding a fuel mass flow to a burner having multiple fuel supply lines; and
varying the distribution of the fuel mass flow to said fuel supply lines dependent on the determined fuel gas properties.

8. A method for operating a gas turbine group, the gas turbine group including a fuel gas supply line and a device for determining fuel gas properties arranged in said fuel gas supply line, the method comprising:
determining at least one fuel gas property;
feeding the determined fuel gas property to a control system of the gas turbine group;
performing control action on the operation of the gas turbine group dependent on the determined fuel gas property, the control action being performed on at least one selected from the group consisting of the distribution of a fuel gas mass flow between different fuel gas outlet openings, a combustion air supply of burners of the gas turbine group, and the injection of inert media into a gas turbine group working fluid;
operating said gas turbine group at a power output;
defining at least one critical value for at least one of the determined fuel gas properties; and
decreasing the power output upon detection of a critical value.

9. The method of claim 8, comprising:
shutting down the gas turbine group upon detection of a critical value.

10. The method of claim 8, comprising:
defining an upper limit value of the $C_{2+}$-alkane content; and
defining any value exceeding said upper limit value as a critical value.

11. The method of claim 4, comprising:
feeding a fuel mass flow to a burner having multiple fuel supply lines; and
varying the distribution of the fuel mass flow to said fuel supply lines dependent on the determined fuel gas properties.

12. The method of claim 8, comprising:
feeding a fuel mass flow to a burner having multiple fuel supply lines; and
varying the distribution of the fuel mass flow to said fuel supply lines dependent on the determined fuel gas properties.

* * * * *